(12) United States Patent
Slawson et al.

(10) Patent No.: US 6,830,347 B2
(45) Date of Patent: Dec. 14, 2004

(54) EYE VIEWING DEVICE COMPRISING EYE CUP

(75) Inventors: Steven R. Slawson, Camillus, NY (US); Chris R. Roberts, Skaneateles, NY (US); Allan I. Krauter, Skaneateles, NY (US); Ervin Goldfain, Syracuse, NY (US)

(73) Assignee: Welch Allyn, Inc, Skaneateles, NY (US)

( * ) Notice: Subject to any disclaimer, the term of this patent is extended or adjusted under 35 U.S.C. 154(b) by 444 days.

(21) Appl. No.: 09/783,224

(22) Filed: Feb. 14, 2001

(65) Prior Publication Data

US 2003/0063386 A1 Apr. 3, 2003

(51) Int. Cl.⁷ .............................. G02B 23/16; A61B 3/00
(52) U.S. Cl. ........................ 359/600; 359/819; 351/219
(58) Field of Search ................................ 359/507–512, 359/600, 800–819, 611; 351/200–247; 600/110, 200, 161–180

(56) References Cited

U.S. PATENT DOCUMENTS

| | | | |
|---|---|---|---|
| 1,605,725 A | * 11/1926 | Herbert, Jr. ................. 351/200 |
| 2,186,206 A | 1/1940 | Posner ........................ 359/611 |
| 3,371,660 A | * 3/1968 | Carlin ........................ 600/452 |
| 3,390,931 A | * 7/1968 | Luming et al. | |
| 3,545,260 A | * 12/1970 | Lichtenstein et al. ....... 351/212 |
| 3,903,871 A | * 9/1975 | Chisum et al. | |
| 3,929,124 A | * 12/1975 | Yablonski et al. | |
| 4,026,591 A | * 5/1977 | Cleaveland ................. 351/219 |
| 4,264,123 A | * 4/1981 | Mabie | |
| 4,907,595 A | * 3/1990 | Strauss ........................ 351/200 |
| 4,930,507 A | * 6/1990 | Krasnicki et al. ........... 128/649 |
| 5,225,932 A | * 7/1993 | Wannagot et al. | |
| 5,255,025 A | * 10/1993 | Volk | |
| 5,662,586 A | * 9/1997 | Monroe et al. | |
| 5,879,289 A | * 3/1999 | Yarush et al. | |
| 6,106,457 A | 8/2000 | Perkins et al. .............. 600/175 |
| 6,190,310 B1 | * 2/2001 | Cook | |

FOREIGN PATENT DOCUMENTS

| | | |
|---|---|---|
| DE | 912 046 | 3/1954 |
| EP | 0 176 169 | 4/1986 |
| WO | 86/01992 | 4/1986 |
| WO | 00/57771 | 10/2000 |

\* cited by examiner

*Primary Examiner*—Thong Q Nguyen
(74) *Attorney, Agent, or Firm*—Wall Marjama & Bilinski LLP

(57) ABSTRACT

The invention is a hand-held eye viewing device adapted to be readily positioned in an operative radial displacement, angular orientation and axial standoff position relative to an eye. The eye viewing device includes an eye cup extending from a patient end of the device having a patient end adapted to be received at a patient's eye orbit. By allowing the eye viewing device to be stabilized against an eye orbit the eye cup eases the task of maintaining an operative position once an operative position has been achieved.

12 Claims, 5 Drawing Sheets

EYE VIEWING DEVICE COMPRISING EYE CUP

BACKGROUND OF THE INVENTION

1. Field of the Invention

The invention relates to eye viewing devices in general and specifically to a hand-held eye viewing device that is adapted to be readily moved into an operative position relative to a patient's eye.

2. Background of the Prior Art

Many types of eye viewing devices require a certain positioning relative to a patient for proper operation. Retinal viewing ophthalmoscopes, in particular should be positioned at a certain radial displacement, angular orientation and axial standoff position relative to a patient's eye for proper operation. The task of moving a retinal viewing ophthalmoscope into an operative position relative to an eye is particularly challenging given that in order to provide viewing of different areas of a retina, such devices should be moved between various angular orientations relative to an eye while maintaining certain radial displacement and axial standoff positions.

The positioning of commercially available hand-held eye viewing devices is customarily controlled entirely by the hand-eye coordination of a physician. During use of a known retinal viewing ophthalmoscope, for example, a physician manually moves the device into an operative position depending upon the image of the retina generated by the device's viewing system at the physician's retina.

Limitations have been observed with this method of positioning an eye viewing device. First, physicians using certain commercially available eye viewing devices have faced difficulty in positioning such devices in an operative position. The difficulty faced in achieving an operative position varies depending upon the particular eye viewing device. It is particularly challenging to position retinal viewing ophthalmoscopes relative to an eye since light rays of both the illumination and imaging system of such devices must pass through a patient's pupil.

In general, the more challenging the task of achieving an operative position, the more difficult the task is of maintaining that operative position once it has been achieved. An operative position of certain eye viewing devices can be lost, for example, with small disturbances in the radial displacement position of the device relative to an eye.

There is a need for an eye viewing device which is adapted to be readily positioned in a desired radial displacement, angular orientation and axial standoff position relative to a patient, and which is adapted to be readily maintained in that desired radial displacement, angular orientation and axial standoff position once that position is attained.

SUMMARY OF THE INVENTION

According to its major aspects and broadly stated the invention is an eye viewing device adapted to be readily positioned in an operative position relative to an eye.

An eye viewing device according to the invention includes an eye cup having patient end adapted to be received at an eye orbit of a patient, the eye orbit being generally defined by an eyebrow and upper cheekbone of a patient. In one aspect of the invention, the outer diameter of the patient end of the eye cup is sized to correspond to a patient's eye orbit. Because a center of a patient eye is located substantially at the center of an eye orbit, the sizing of the patient end outer diameter corresponding to an eye orbit operates to aid in the radial displacement positioning of the device.

In another aspect, the eye cup is made deformable so that contact of the eye cup with a patient alerts a physician that the device is approaching an operative axial standoff position. Making the eye cup deformable also enhances patient comfort.

In yet another aspect of the invention, the eye cup is made so that the eye viewing device can pivot about a pivot point near the patient end of the eye cup to allow adjustment of the eye viewing device's angular orientation position relative to an eye to visualize various areas of the retina. Forming the eye cup so that the eye viewing device pivots about a pivot point toward the eye cup's patient end allows adjustment of an eye viewing devices's angular orientation without substantial disruption of the positioning of the device's illumination and viewing axes relative to a pupil center (i.e., without disruption of the radial position) and therefore without movement of the device from an operative position.

In addition to aiding in the positioning of an eye viewing device relative to a patient, the eye cup prevents ambient light rays from reaching a patient's eye, thereby substantially eliminating sources of external glare. Furthermore, because the eye cup allows the eye viewing device to be stabilized against an eye orbit during eye viewing, the eye cup eases the task of maintaining an operative viewing position after such an operative position is achieved.

These and other details, advantages and benefits of the present invention will become apparent from the detailed description of the preferred embodiment hereinbelow.

DESCRIPTION OF THE DRAWINGS

For a fuller understanding of the nature and objects of the invention, references should be made to the following detailed description of a preferred mode of practicing the invention, read in connection with the accompanying drawings, in which.

DETAILED DESCRIPTION

The task of moving an eye viewing device into an operative position relative to a patient's eye is a challenging one for certain types of eye viewing devices. Retinal viewing ophthalmoscopes, in particular, must be positioned at specific radial displacement and axial standoff positions relative to a patient's eye in order to achieve operative illumination and imaging of a retina. Retinal viewing ophthalmoscopes also must be positioned at a specific angular orientation relative to an eye to allow viewing of a particular area of a retina not observable in the central view.

The term "radial displacement" herein refers to the radial distance between a patient's pupil center and an imaging axis, $a_i$, of device 10. The term "angular orientation" herein refers to the angle formed between the imaging axis of device 10 and the axis of a patient's pupil, while the term "axial standoff" herein refers to the spacing between device 10 and a patient's eye along the imaging axis, $a_i$.

Figure 1A:
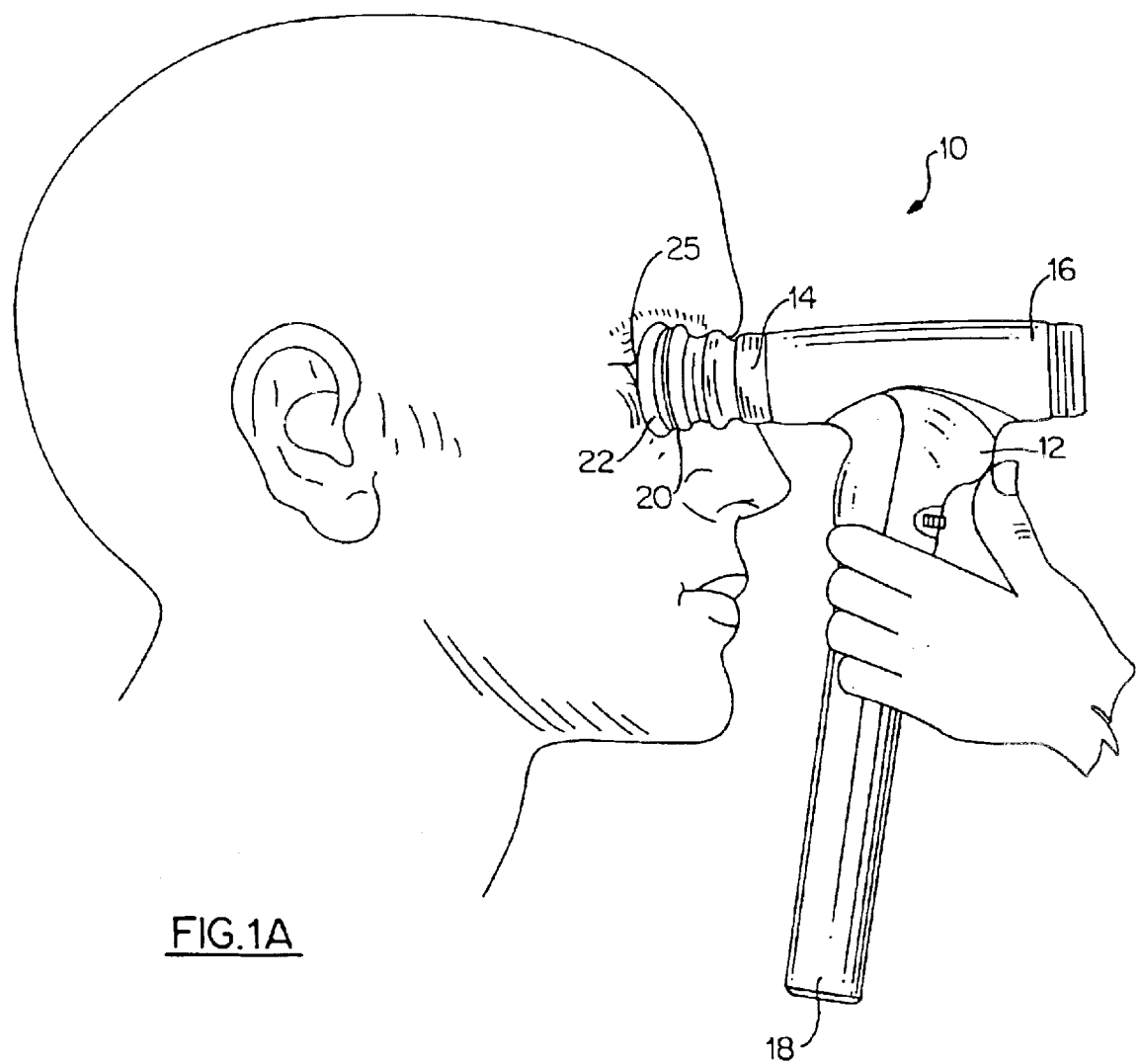
FIG. 1A is a perspective view of an eye cup-equipped eye viewing device as seen in use.
Figure 1B:
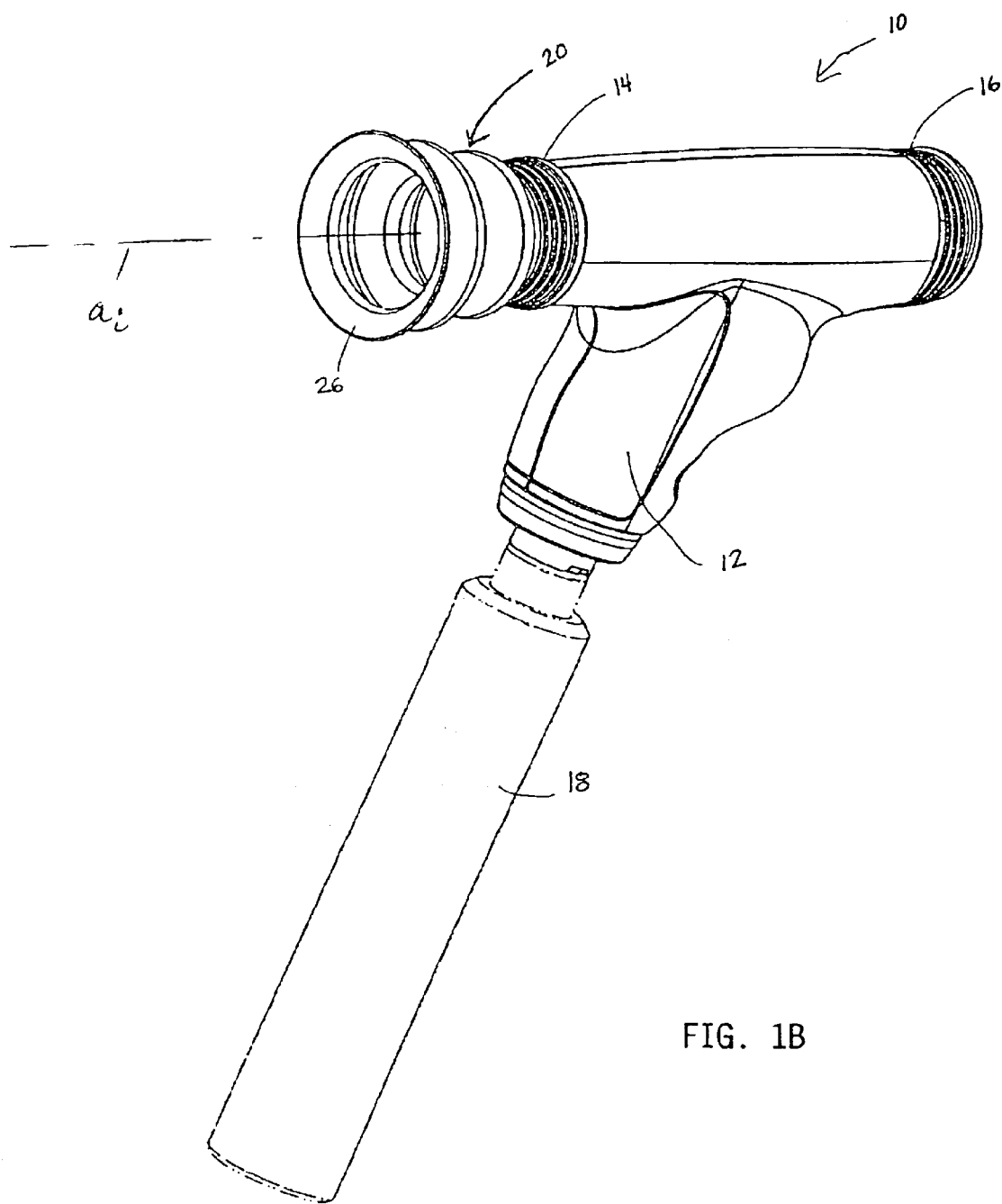
FIG. 1B is another perspective view of an eye viewing device according to the invention.

An eye viewing device adapted to be readily positioned in a desired radial displacement, angular orientation and axial standoff position relative to a patient's eye is described with reference to FIGS. 1A–3C. As seen in FIG. 1A, device 10 includes a housing 12 which comprises patient end 14, a physician or observer end 16, and a handle 18. According to the invention, patient end 14 has disposed thereon an eye cup 20 which as will be explained herein is useful in achieving proper radial displacement, angular orientation, and axial offset positioning of device 10 relative to a patient's eye.

In use, a physician moves device 10 toward a patient's eye orbit 25 until bottom surface 26 (FIG. 1B) of patient end 22 of eye cup 20 is substantially in contact with an eye orbit 25 of a patient. When device 10 is a retinal viewing ophthalmoscope, a physician during the course of moving device 10 into an operative position, further attempts to position the device such that a "spot" retinal image (known as the "red reflex" image) is continuously generated by the device's viewing system.

Referring to one aspect of the invention, the outer diameter OD of eye cup patient end 22 should be sized to substantially correspond to an eye orbit 25 of a patient (FIG. 1A). Because a patient's pupil 32 (FIG. 3A) is located substantially at a center of an eye orbit, contact with an eye orbit 25 of an eye cup having an outer diameter substantially corresponding to orbit 25 radially places device 10 such that the axis, $a_c$, (FIG. 2F) of eye cup 20 at patient end 22 passes substantially through a center of a patient's pupil. Because eye cup 20 is normally disposed on housing 12 such that eye cup axis, $a_c$, substantially coincides with the imaging axis, $a_i$, of device 10, contact of eye cup 20 with an eye orbit operates to align the device's imaging axis with a patient's pupil (i.e. with minimal radial displacement).

Figure 2A:
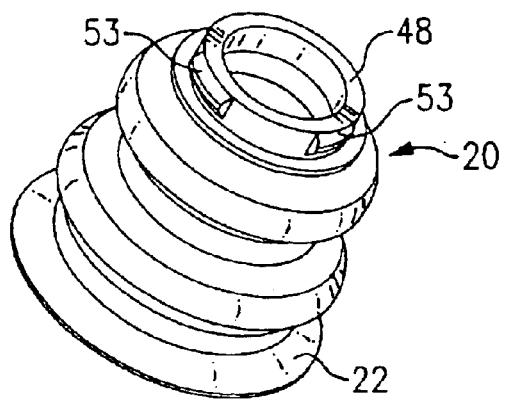
FIG. 2A is a perspective view of an eye cup according to the invention.
Figure 2B:
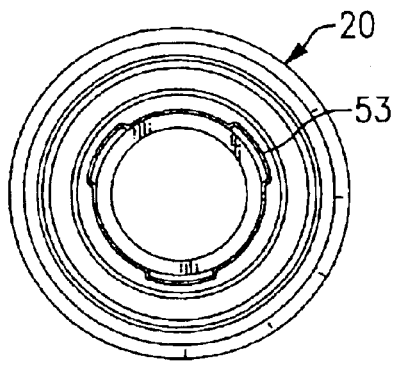
FIG. 2B is a top view of an eye cup according to the invention.
Figure 2C:
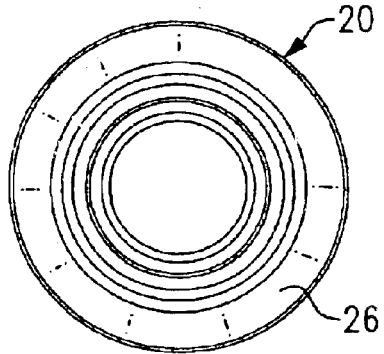
FIG. 2C is a bottom view of an eye cup according to the invention.
Figure 2D:
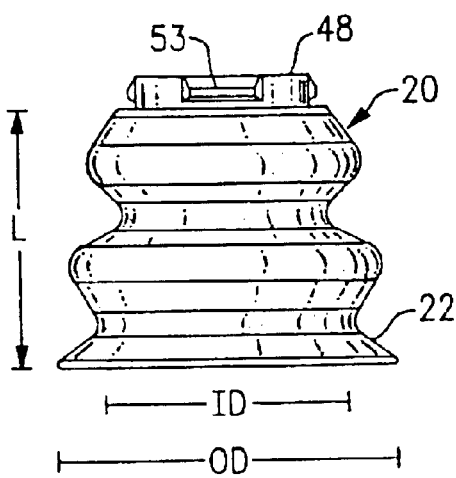
FIG. 2D is a side view of an eye cup according to the invention.

In another aspect of the invention, eye cup 20 is configured to have an exposed length L, as seen in FIG. 2D, such that contact of cup 20 with an eye orbit alerts a physician that device 10 is approaching or is at a proper axial standoff position from a patient's eye.

Figure 2E:
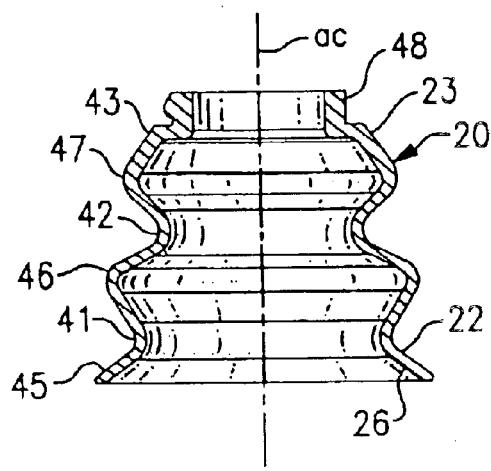
FIG. 2E is a cross-sectional side view of an eye cup according to the invention.
Figure 2F:
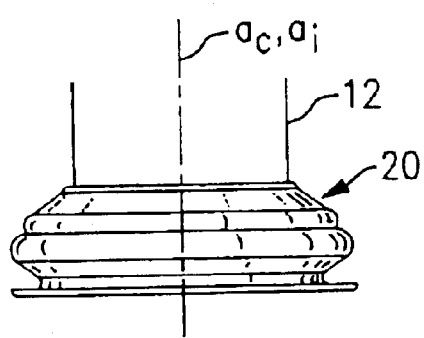
FIG. 2F is a side view of an eye cup according to the invention in a deformed, or compressed configuration.
Figure 2G:
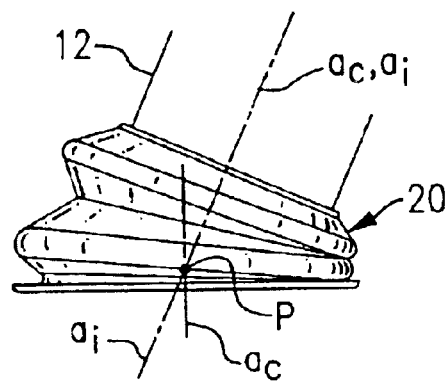
FIG. 2G is a side view of an eye cup with a change of angular orientation according to the invention.

For use with certain eye viewing devices (such as corneal viewing devices or dilated-pupil retinal viewing devices) eye cup 20 can be substantially rigid such that the proper axial standoff position of a device relative to an eye is achieved when eye cup 20 first comes in contact with orbit 25. However, for use with certain eye viewing devices that require relatively precise spacing of device 10 to an eye it is preferred that eye cup 20 is made deformable. When eye cup 20 is configured to be deformable, contact of eye cup 20 with an eye orbit 25 alerts a physician that the device is approaching a proper axial standoff position. An operative axial standoff position of device having a deformable eye cup is achieved when eye cup 20 is in a deformed configuration, as is shown in FIGS. 2F and 2G. Making eye cup 20 deformable adapts the eye cup for variations in eye configurations between eyes of different patients and increases patient comfort. Eye cup 20 can be made deformable by configuring eye cup 20 in a bellows configuration as is indicated in FIGS. 1A–2G and which will be described in greater detail hereinbelow.

Figure 3A:
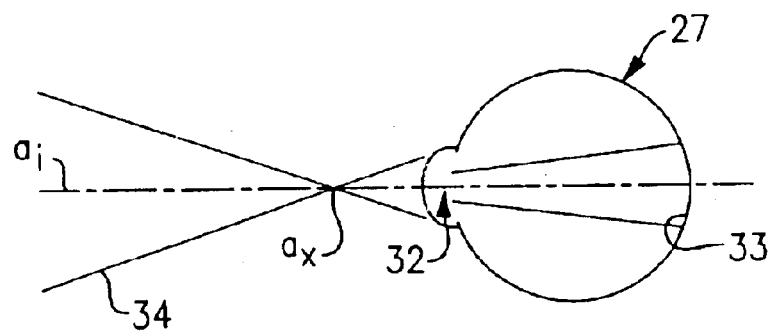
FIG. 3A is a diagram illustrating a conical illumination eye viewing device at a first axial standoff position relative to an eye as exists during the entry process.
Figure 3B:
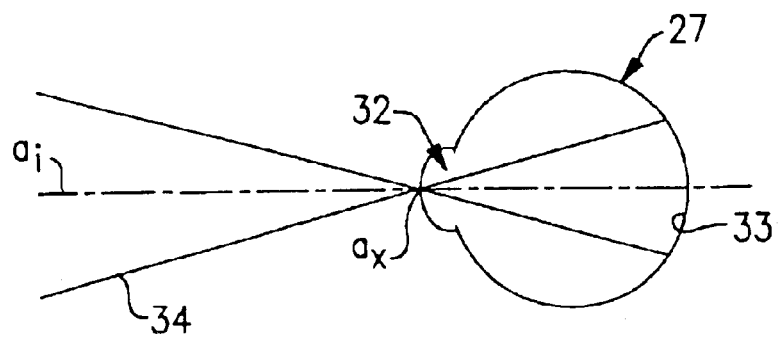
FIG. 3B in a diagram illustrating a conical illumination eye viewing device at a second axial standoff position relative to an eye, typical of an operative position.

Axial standoff positioning between an eye viewing device 10 and an eye must be substantially precise in retinal viewing devices having conical illumination as can be seen by comparison of FIGS. 3A and 3B. Conical illumination systems generate a cone of light having light rays that converge at an apex and diverge thereafter. FIG. 3A shows a cone of light illumination in which apex, ax, of the cone of light 34 is spacely apart from a pupil 32 while FIG. 3B shows a cone of light illumination in which apex, ax, of cone of light 34 is positioned at a pupil 32. Comparing to FIGS. 3A and 3B it can be seen that illumination of a retina illuminated by a conical illumination system improves when apex, ax, of the conical illumination is substantially positioned at a pupil. In the specific embodiment of the deformable configured eye cup shown in FIGS. 1A–3G, apex, ax, of cone of light 34 is at a position forward of pupil 32, indicated in FIG. 3A when eye cup 20 first contacts an eye orbit 25, and at a position substantially within pupil 32 when eye cup 20 is in an operative deformed configuration. Examples of retinal viewing ophthalmoscopes having conical illumination systems are described in commonly assigned U.S. Pat. No. 6,065,837, and concurrently filed Application Ser. No. 09/444,161 entitled "Eye Viewing Device for Retinal Viewing through Undilated Pupil," both of which are incorporated herein by reference.

Referring to further aspects of eye cup 20, eye cup 20 preferably is adapted to allow device 10 to be readily positioned at varying angular orientations relative to an eye. It is common to adjust the field of view of many types of eye viewing devices by adjusting the device's angular orientation relative to an eye 27 (FIG. 3A). For example, different regions of a retina 33 can be viewed through a pupil with a retinal viewing ophthalmoscope by adjusting the angular orientation of the ophthalmoscope while maintaining the imaging axis of the device in a position substantially centered in a pupil 32.

Eye cup 20 can be made to allow adjustment of device angular orientation relative to an eye by configuring eye cup 20 such that device 10 can be pivoted about a point, P, on eye cup axis, $a_c$. As indicated in FIGS. 2F and 2G, eye cup 20 can be made so that device 10 is moveable between a first configuration indicated in FIG. 2F in which the axis, $a_c$, of eye cup 20 substantially coincides with the imaging axis, $a_i$, of device throughout the length of eye cup 20 and a second configuration indicated in FIG. 2G in which eye cup axis, $a_c$, is pivoted about a pivot point P.

The imaging system of a retinal viewing ophthalmoscope generates a retinal image when the device's imaging axis, $a_i$, passes through a patient's pupil 32. Eye cup 20 is disposed on housing 12 so that eye cup axis, $a_c$, toward eye cup upper end 23 substantially coincides with the device's imaging axis, $a_i$. Accordingly, it can be seen that configuring eye cup 20 so that device 10 pivots about a pivot point, P, proximate a pupil 32, allows retinal imaging to be maintained throughout the moving of the ophthalmoscope from an angular orientation position normal to a pupil 32 to a position oblique relative the pupil.

The bellows-configured eye cup described with reference to FIGS. 2A–2G can be made to pivot at a pivot point proximate a pupil 32 by configuring eye cup 20 to have proportionately thinner material at the bellows sections toward patient end 22 of eye cup 20. As seen in the cross-sectional view of FIG. 2E, the walls of eye cup 20 are formed gradually thinner toward patient end 22 to produce pivoting toward patient end 22. First bellows section 41 has a smaller thickness than second bellows section 42 which has a smaller thickness than third bellows section 43. The walls 47 of the third bellows 43 are substantially thicker than the walls 45 and 46 of the first and second bellows 41, and 42, respectively. The configuration shown in FIG. 2E provides an eye cup which pivots substantially toward patient end 22 when eye cup 20 is in an axially deformed or compressed configuration and the device is moved angularly.

Referring to a still further aspect of the invention, eye cup 20 should be made substantially opaque so that eye cup 20 substantially blocks ambient light rays from reaching a patient's eye. By blocking ambient light rays, eye cup 20 operates to substantially eliminate this source of external glare.

Further, referring to FIG. 1A showing a device according to the invention in use, it can be seen that eye cup 20 allows device 10 to be stabilized against a patient's eye orbit during eye viewing. Accordingly, in addition to aiding the task of positioning device 10 in an operative position, eye cup 20 eases the task of maintaining an operative position once an operative position has been achieved.

Additional specific structural details of a preferred embodiment of eye cup 20 are described with reference again to FIGS. 2A–2G. Bottom surface 26 of cup 20, which is the patient contact surface, preferably defines a flange configuration as is best seen by bottom view FIG. 2C. The flange-shaped bottom surface enhances patient comfort and, by providing for substantial contact of cup 20 with eye orbit 25, encourages radial stabilization of eye cup 20 on eye orbit 25. While bottom surface 26 is substantially circular, it is contemplated that the bottom surface 26 can be configured in other configurations, including configurations that more precisely approximate the actual shape of a patient's eye orbit.

While eye cup outer diameter OD is sized to correspond to an eye orbit as explained previously, inner diameter ID of cup 20 is sized so as not to substantially interfere with a patient's eyelashes during blinking or to interfere with the illumination and imaging performance of the eye viewing device. Eye cup 20 can have an outer diameter of between about 35 mm and 55 mm and an inner diameter of between about 20 mm and about 40 mm. In the embodiment of FIGS. 2A–2G eye cup 20 has an outer diameter of about 45 mm and an inner diameter of about 32 mm at bottom surface 26.

Eye cup 20 may be made from moldable elastomeric or plastic material that is biocompatible, cleanable, sterilizable, and of low durometer. A preferred material for eye cup 20 is silicone.

Figure 4A:
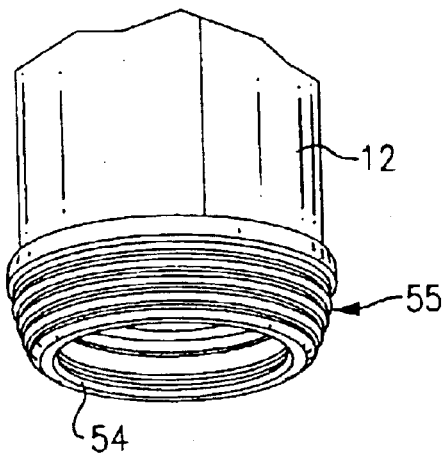
FIG. 4A is a perspective view of a device housing patient end.
Figure 4B:
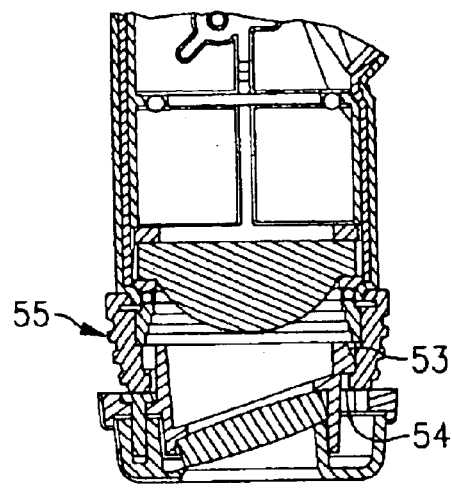
FIG. 4B is a cross-sectional side view of a magnifier lens assembly engaged in a device housing.

In the particular embodiment of FIGS. 2A–2G, eye cup 20 includes a top connector section 48 as best seen in FIG. 2A, which adapts eye cup 20 to be detachably attached to an eye viewing device housing 12. Preferably, eye cup 20 is made to be detachably held in place in housing 12 ribs that deform during engagement with or disengagement from, the housing. In the specific embodiment shown, top connector section 48 includes ribs 53 adapted to be received in complementarily formed lip 54 of housing 12, as seen in FIG. 4A. Lip 54 may be part of a nose interface 55 forming patient end 14 of housing 12. Nose interface 55 may comprise a relatively stiff elastomeric material. When nose interface 55 comprises resilient elastomeric material, attachments received in lip 54 can be formed from either a flexible material or from a substantially rigid material such as metal or plastic. As alluded to previously, eye cup 20 should be formed so that upper end 23 (FIG. 2E) of eye cup 20 is held substantially stable in housing 12 toward upper end 23 but pivots readily about a pivot point, P (FIG. 2G), along axis, $a_c$, toward patient end 22.

Figure 4C:
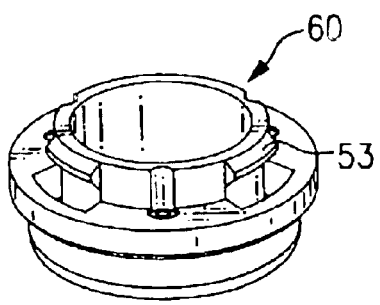
FIG. 4C is a perspective view of a magnifier assembly attachment or filter assembly attachment according to the invention.
Figure 4D:
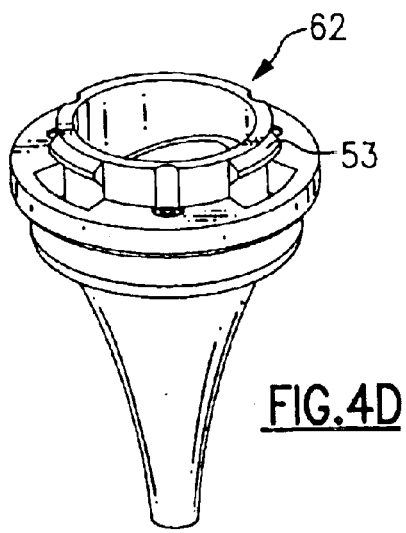
FIG. 4D is a perspective view of an otoscope attachment according to the invention.
Figure 4E:
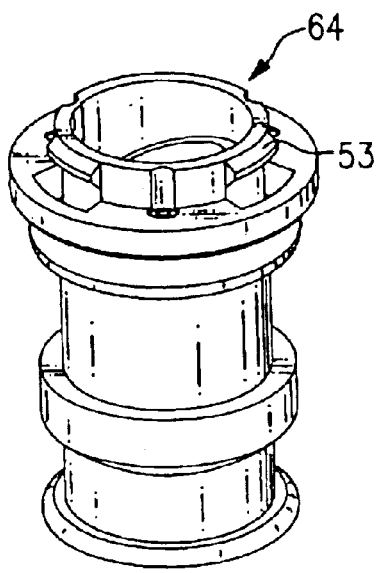
FIG. 4E is a perspective view of an episcope attachment according to the invention.

Other attachments may be detachably attached to housing 12. For example, shown in FIG. 4C is a magnifier lens assembly 60 which may be detachably attached to housing 12 in the manner of eye cup 20. With proper sizing of the lens or lenses of assembly 60, attaching magnifier lens assembly 60 to housing 12 allows device 10 to be used as a cornea viewing device. Other attachments which may be detachably attached to housing 12 in substantially the manner of eye cup 20 or magnifier lens assembly 60 includes optical filter attachments, otoscope attachments, and episcope attachments. A filter assembly attachment for attachment to housing 12 may comprise the general configuration of assembly 60 as show in FIG. 4C. An exemplary otoscope assembly attachment 62 is shown in FIG. 4D while an exemplary episcope assembly attachment 64 is shown in FIG. 4E. The above assembly attachments 60, 62, 64 have ribs 53, allowing attachments to be detachably received by housing 12 in substantially the manner of eye cup 20.

While the present invention has been explained with reference to the structure disclosed herein, it is not confined to the details set forth and this invention is intended to cover any modifications and changes as may come within the scope of the following claims:

What is claimed is:

1. An eye viewing device comprising:
    a housing having a patient end and an observer end;
    an eye cup disposed at said patient end, said eye cup having a patient end being sized such that its outer edge substantially corresponds to an eye orbit of a patient, wherein said eye orbit is generally defined by an eyebrow and an upper portion of a cheekbone of said patient; and
    wherein said eye cup comprises a plurality of deformable bellows.

2. An eye viewing device comprising:
    a housing having a patient end and an observer end;
    an eye cup disposed at said patient end, said eye cup having a patient end being sized such that its outer edge substantially corresponds to an eye orbit of a patient, wherein said eye orbit is generally defined by an eyebrow and an upper portion of a cheekbone of said patient; and
    wherein said eye cup is adapted to pivot substantially about a patient end of said eye cup.

3. An eye viewing device comprising:
    a housing having a patient end and an observer end;

an eye cup disposed at said patient end, said eye cup having a patient end being sized such that its outer edge substantially corresponds to an eye orbit of a patient, wherein said eye orbit is generally defined by an eyebrow and an upper portion of a cheekbone of said patient; and wherein said eye cup is adapted to pivot substantially about a patient's pupil when said device is in an operative position.

4. An eye viewing device comprising:

a housing having a patient end and an observer end;

an eye cup disposed at said patient end, said eye cup having a patient end being sized such that its outer edge substantially corresponds to an eye orbit of a patient, wherein said eye orbit is generally defined by an eyebrow and an upper portion of a cheekbone of said patient; and wherein said eye cup comprises a plurality of bellows wherein walls of said bellows are formed progressively thinner toward said patient end of said eye cup so that pivoting occurs substantially toward a patient end of said eye cup.

5. An eye viewing device comprising:

a housing having a patient end and an observer end;

an eye cup disposed at said patient end, said eye cup having a patient end being sized such that its outer edge substantially corresponds to an eye orbit of a patient, wherein said eye orbit is generally defined by an eyebrow and an upper portion of a cheekbone of said patient; and wherein said eye cup comprises a plurality of bellows, wherein walls of said bellows are formed progressively thinner toward said a patient end of said eye cup so that pivoting occurs substantially about a patient's pupil when said device is in an operative position.

6. An apparatus for aiding in the positioning of an eye viewing device relative to a patient, said apparatus comprising:

a device end adapted to be attached to a patient end of said eye viewing device;

a patient end adapted to be received at an eye orbit of said patient, wherein said patient end of said apparatus is sized such that its outer edge corresponds to an eye orbit of a patient, said eye orbit being generally defined by an eyebrow and an upper portion of a cheekbone of said patient and wherein said apparatus comprises a plurality of deformable bellows.

7. An apparatus for aiding in the positioning of an eye viewing device relative to a patient, said apparatus comprising:

a device end adapted to be attached to a patient end of said eye viewing device;

a patient end adapted to be received at an eye orbit of said patient, wherein said patient end of said apparatus is sized such that its outer edge corresponds to an eye orbit of a patient, said eye orbit being generally defined by an eyebrow and an upper portion of a cheekbone of said patient; and wherein said apparatus adapted to pivot substantially about said patient end of said apparatus.

8. An apparatus for aiding in the positioning of an eye viewing device relative to a patient, said apparatus comprising:

a device end adapted to be attached to a patient end of said eye viewing device;

a patient end adapted to be received at an eye orbit of said patient, wherein said patient end of said apparatus is sized such that its outer edge corresponds to an eye orbit of a patient, said eye orbit being generally defined by an eyebrow and an upper portion of a cheekbone of said patient; and wherein said apparatus is adapted to pivot about a pivot point defined substantially about a patient's pupil when said device is in an operative position.

9. An apparatus for aiding in the positioning of an eye viewing device relative to a patient, said apparatus comprising:

a device end adapted to be attached to a patient end of said eye viewing device;

a patient end adapted to be received at an eye orbit of said patient, wherein said patient end of said apparatus is sized such that its outer edge corresponds to an eye orbit of a patient, said eye orbit being generally defined by an eyebrow and an upper portion of a cheekbone of said patient; and wherein said apparatus comprises a plurality of bellows wherein walls of said bellows are formed progressively thinner toward said patient end of said apparatus so that a pivot point is defined substantially toward a patient end of said apparatus.

10. An apparatus for aiding in the positioning of an eye viewing device relative to a patient, said apparatus comprising:

a device end adapted to be attached to a patient end of said eye viewing device;

a patient end adapted to be received at an eye orbit of said patient, wherein said patient end of said apparatus is sized such that its outer edge corresponds to an eye orbit of a patient, said eye orbit being generally defined by an eyebrow and an upper portion of a cheekbone of said patient; and wherein said eye cup comprises a plurality of bellows, wherein walls of said bellows are formed progressively thinner toward said patient end of said apparatus so that a pivot point of said apparatus is defined substantially about a patient's pupil when said device is in an operative position.

11. A method for positioning an eye viewing device in an operative position relative to a patient, said eye viewing device having a patient end, said method comprising the steps of:

providing a spacer on said patient end of said eye viewing device;

moving said device toward said patient at least until said spacer contacts said patient at the eyebrow and upper cheekbone area; and wherein said providing step includes the step of providing a spacer configured to pivot toward a patient end of said spacer so that said spacer facilitates angular adjustment of said device while an operative position is maintained.

12. A retinal viewing device comprising:

a housing having an operator end and a patient end;

an attachment interface formed at said patient end adapted to detachably receive an attachment;

said attachment consisting of a lens assembly and an optical filter assembly; and wherein said attachment interface comprises a lip, and wherein said attachment comprises at least one rib.

* * * * *